(12) United States Patent
Coniglio et al.

(10) Patent No.: US 6,202,991 B1
(45) Date of Patent: Mar. 20, 2001

(54) BUBBLE HUMIDIFIER WITH VALVE INLET FOR SUPPLYING LIQUID THEREIN

(76) Inventors: Nicholas Edward Coniglio, 22 River Rd., Apt. #402, Pittsburgh, PA (US) 15238; Harry Francis Mellon, Jr., 490 Woodland Rd., Pittsburgh, PA (US) 15237

(*) Notice: Subject to any disclaimer, the term of this patent is extended or adjusted under 35 U.S.C. 154(b) by 0 days.

(21) Appl. No.: 09/243,907

(22) Filed: Feb. 3, 1999

(51) Int. Cl.[7] ............................................. B01F 3/04
(52) U.S. Cl. .................. 261/121.1; 261/122.1; 261/124; 261/DIG. 65; 128/203.12
(58) Field of Search .................. 261/74, 121.1, 261/122.1, 124, DIG. 65; 128/203.12

(56) References Cited

U.S. PATENT DOCUMENTS

| | | | |
|---|---|---|---|
| 529,684 | * 11/1894 | Rogers | 261/74 |
| 1,098,623 | * 6/1914 | Haeusler | 261/74 |
| 3,583,685 | * 6/1971 | Boerger et al. | 261/121.1 |
| 3,767,172 | * 10/1973 | Mills | 261/122.1 |
| 3,982,095 | * 9/1976 | Robinson | 261/122.1 |
| 4,101,611 | * 7/1978 | Williams | 261/DIG. 65 |
| 5,505,236 | * 4/1996 | Grabenkort et al. | 128/203.12 |

* cited by examiner

Primary Examiner—C. Scott Bushey
(74) Attorney, Agent, or Firm—James Ray & Associates

(57) ABSTRACT

A bubble humidifier for humidifying gas bubbled through water contained in a container member prior to this gas being sent to a patient is provided. The bubble humidifier includes a container member having a lid, a gas inlet member connected to a gas source, a member for transporting the gas from the gas inlet member into the liquid, and a gas outlet member which feeds the humidified gas to the patient. A valve inlet member is associated with the humidifier unit and allows for the addition of liquid, which humidifies the gas, into the humidifier unit without disassembling the humidifier unit.

23 Claims, 6 Drawing Sheets

BUBBLE HUMIDIFIER WITH VALVE INLET FOR SUPPLYING LIQUID THEREIN

FIELD OF THE INVENTION

The present invention relates, in general, to bubble humidifiers for humidifying gas, and, more particularly, the present invention relates to a bubble humidifier for humidifying a gas which is sent to a patient and, still more particularly, the present invention relates to a bubble humidifier which includes a valve inlet therein such that a humidifying liquid, such as water, may be added to the humidifier unit without disassembling the humidifier unit.

BACKGROUND OF THE INVENTION

Bubble humidifiers are common devices used by patients having lung difficulties for humidifying a gas, such as oxygen, before the gas is sent to the patients. Often, patients require daily oxygen treatments, thus it is necessary to humidify the gas so as to prevent drying of the patients mucous membrane. Drying of mucous membranes can cause serious health problems because the patient becomes susceptible to germs, bacteria, and infection. Due to rising costs in the medical industry, many patients are currently administering the oxygen treatments to themselves at home. Hence, the disposable single patient use bubble humidifier has become a commonly purchased product in the home health care industry.

A commonly used disposable single patient use bubble humidifier comprises a container for holding a humidifying liquid, such as water, and a lid for closing the container. The lid includes a gas inlet which is capable of being attached to a gas source, such as oxygen, a means communicating with the gas inlet for transporting the gas into the liquid in the container to cause the gas to become humidified, and a gas outlet which sends the humidified gas via tubing to the patient. These devices also typically include a safety valve which activates to vent excess gas within the container should an obstruction occur in the tubing which feeds the humidified gas to the patient. Typically the lid is threadedly engageable with the container so that water, or humidifying liquid, can be added to the container as the supply therein becomes depleted during use.

Home health care providers often make service calls to their patients should the patients encounter any difficulty with their equipment. In the case of these disposable single patient use bubble humidifiers, unnecessary service calls are being made because the patients have difficulty reassembling the unit after they have added the humidifying liquid to the container. This difficultly is especially prevalent in patients who have physical impairments, such as Arthritis, Parkinson's and the like, that prevent them from manipulating the components of the humidifier, specifically screwing the lid onto the container.

Another disadvantage in the design of the currently used disposable single patient use humidifier is that the patient may not get a sufficient seal between the lid and the container, causing the gas to leak from the container resulting in the patient not receiving their prescribed flow of oxygen deleteriously affecting the patient's long-term health. A further disadvantage is that the patient could accidentally drop the container with the humidifying liquid therein, spilling its contents during reassembly of the unit. Any or all of these disadvantages could be a disincentive for the patient to use the bubble humidifier during their oxygen treatments. This, in turn, can cause other health care problems from infections due to drying out of the patient's mucous membranes.

SUMMARY OF THE INVENTION

An object of the present invention is to provide a bubble humidifier for humidifying a gas which is sent to a patient wherein the bubble humidifier includes a means for easily adding a humidifying liquid therein.

It is a further object of the invention to provide a bubble humidifier which includes a valve inlet therein such that a humidifying liquid, such as water, may be added to the humidifier unit without disassembling the humidifier unit.

It is yet another object of the invention to provide a bubble humidifier design which reduces the number of service calls being made to home health care patients.

It is another object of the invention to provide a means for retrofitting currently used bubble humidifiers with a one way valve inlet such that a humidifying liquid may be added to these currently used bubble humidifiers in order to obtain any and/or all of the advantages, as enumerated above, in an economical manner.

Briefly, and in accordance with the forgoing objects, the invention comprises a bubble humidifier for humidifying a gas sent to a patient comprising a container member including a top portion, bottom wall, and at least one peripheral sidewall defining a chamber capable of containing a liquid therein, a lid engageable with the container member, a gas inlet means associated with the lid which is also attached to a gas source, a means within the container member for transporting gas fed from the gas inlet means to the liquid to cause this gas to become humidified, a gas outlet means associated with the lid which sends the humidified gas to a patient, and a valve means, preferably a one way valve means, associated with the container member to enable liquid to be added into this container member. The valve means for allowing the application of the humidifying liquid into the container member can be provided on the lid, the container member, or on a separate insert member which may be positioned between and engaged with the lid and the container member.

The invention also includes a method of retrofitting currently used bubble humidifiers with a valve for allowing the application of a humidifying liquid therein by providing an insert member having an open top portion, an open bottom portion, and at least one peripheral sidewall which can be positioned between the top portion of the container member and the bottom portion of the lid. Provided on the at least one peripheral sidewall of this insert member is a valve, preferably a one way valve, which enables the application of liquid into the container member of the bubble humidifier.

Although a number of specific objects and advantages of the present invention have been described in some detail above, various other objects and advantages of the inventive bubble humidifier including a valve means enabling the application of humidifying liquid into the bubble humidifier without disassembly of the humidifier will become much more readily apparent to those persons who are skilled in the art from the following more detailed description of the invention, particularly, when such description is taken in conjunction with both the attached drawing figures and with the appended claims.

DETAILED DESCRIPTION OF THE DRAWINGS

Figure 1:
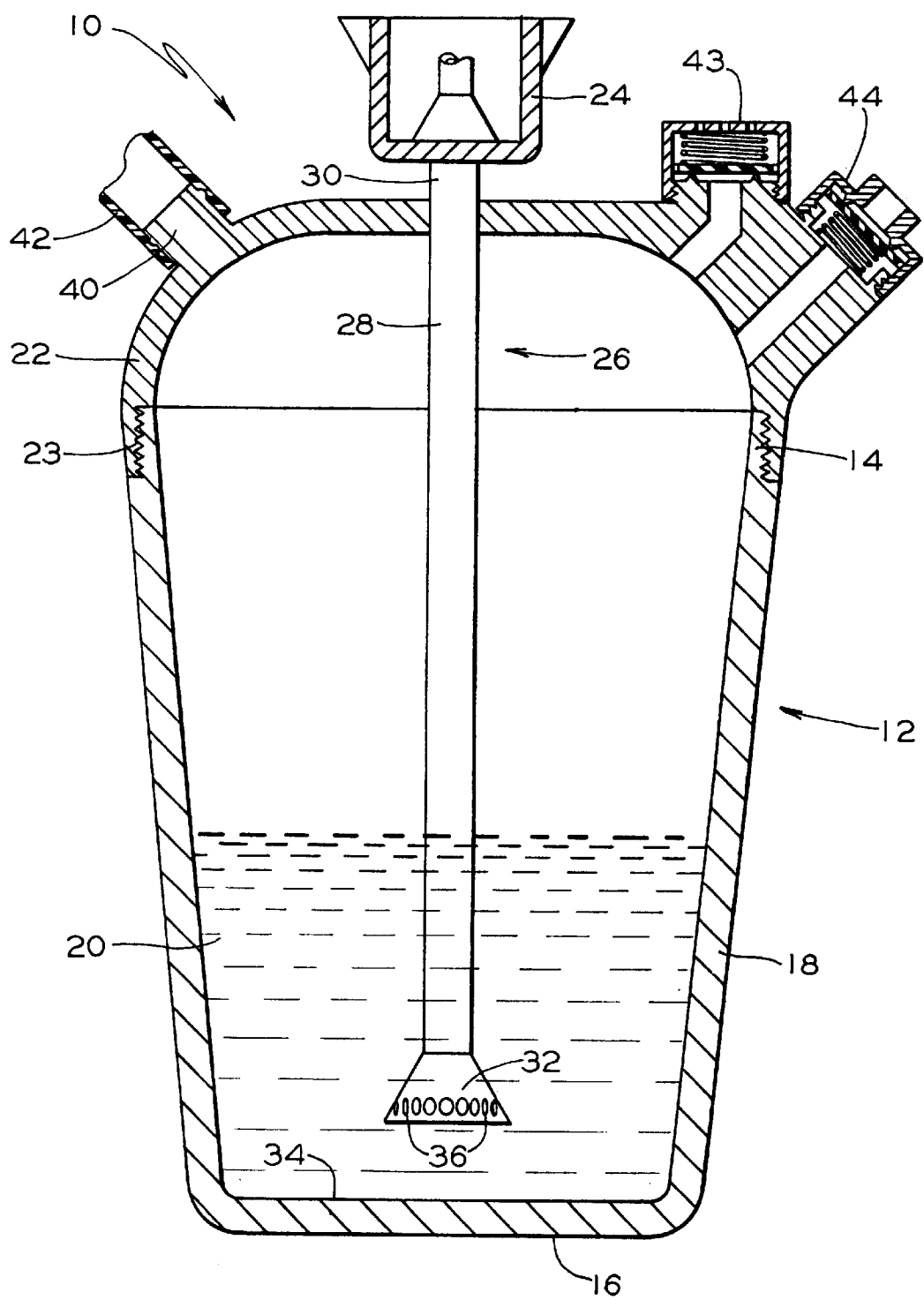
FIG. 1 is a cross-sectional view of a bubble humidifier including a liquid valve inlet means according to a first embodiment of the invention.

Prior to proceeding to the more detailed description of the various embodiments of the instant invention, it should be pointed out that, for the sake of clarity, identical components which have identical functions have been identified with identical reference numerals throughout the several views that have been illustrated in the drawings.

Figure 2:
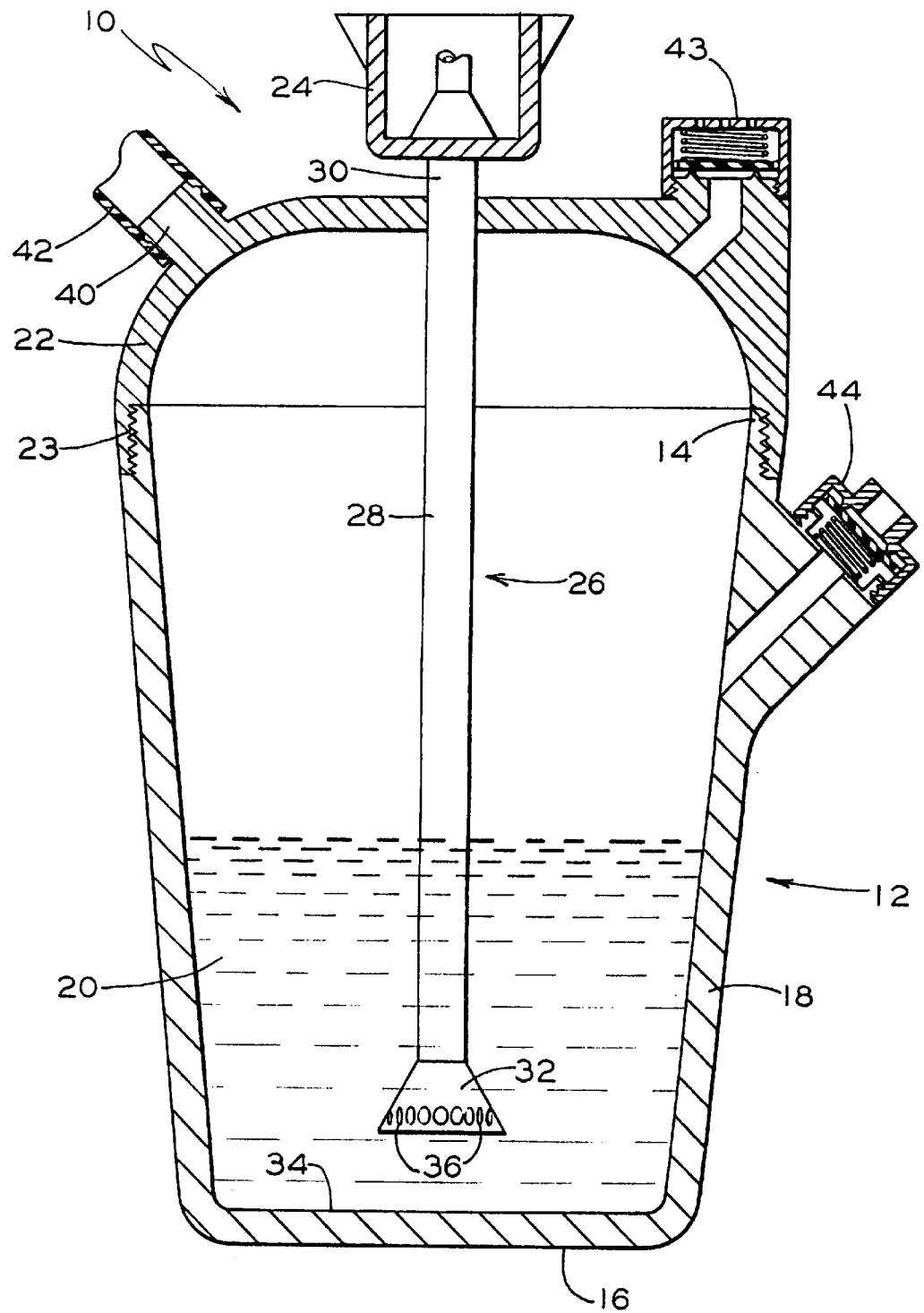
FIG. 2 is a cross-sectional view of a bubble humidifier including a liquid valve inlet means according to a second embodiment of the invention.
Figure 3:
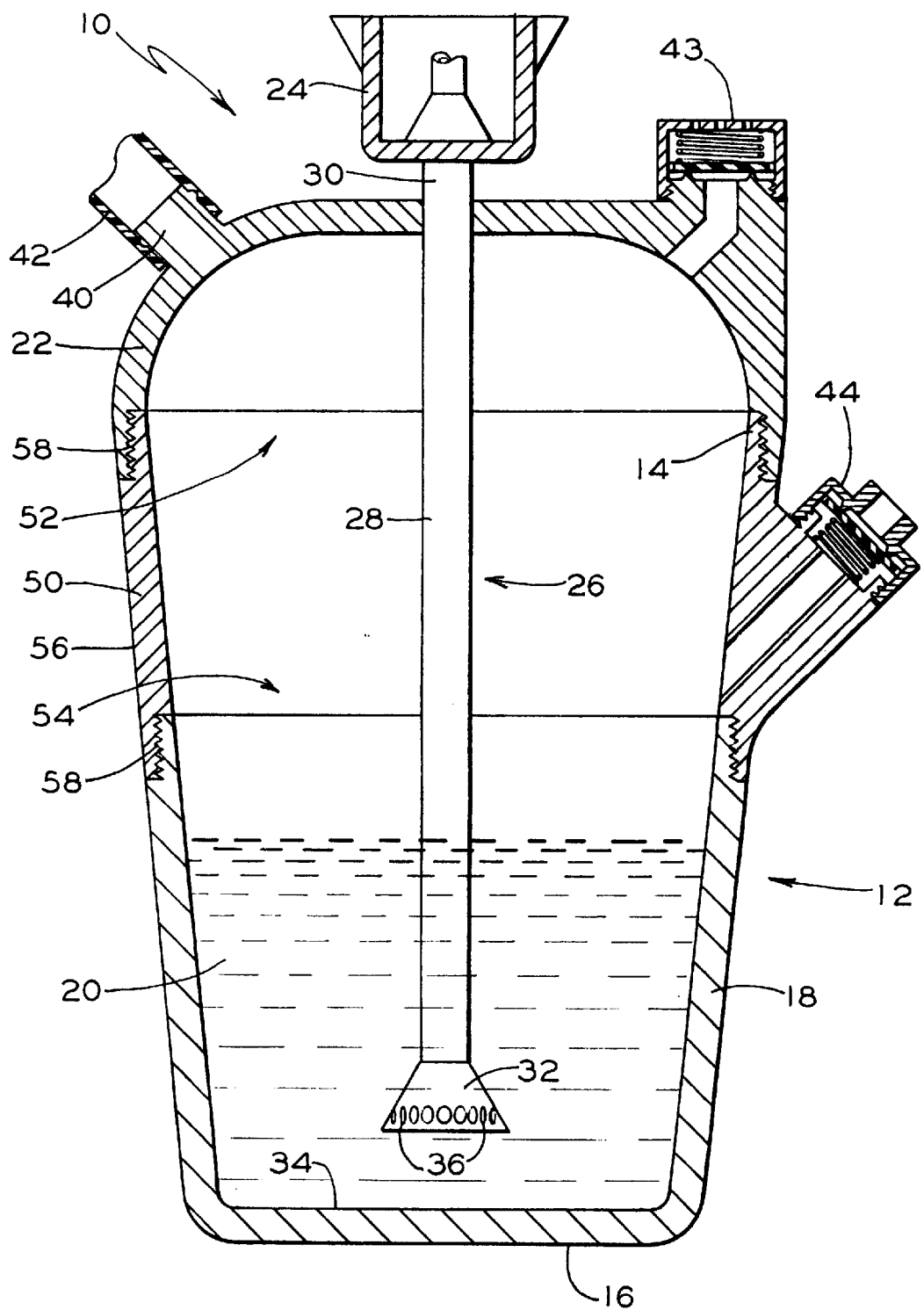
FIG. 3 is a cross-sectional view of a bubble humidifier including a liquid valve inlet means according to a third embodiment of the invention.

Now reference is made, more particularly, to the drawing FIGS. 1–3. Illustrated therein are the essential components of a bubble humidifier, generally designated as 10, used to humidify a gas prior to this gas being sent to a patient.

The bubble humidifier 10 includes a container member, generally designated 12, including a top portion 14, bottom wall 16, and at least one peripheral sidewall 18 defining a chamber capable of containing a liquid 20 therein. Water is typically used as the humidifying liquid, however, any other well known liquid capable of humidifying the gas prior to this gas being sent to the patient may be used.

Figure 4:
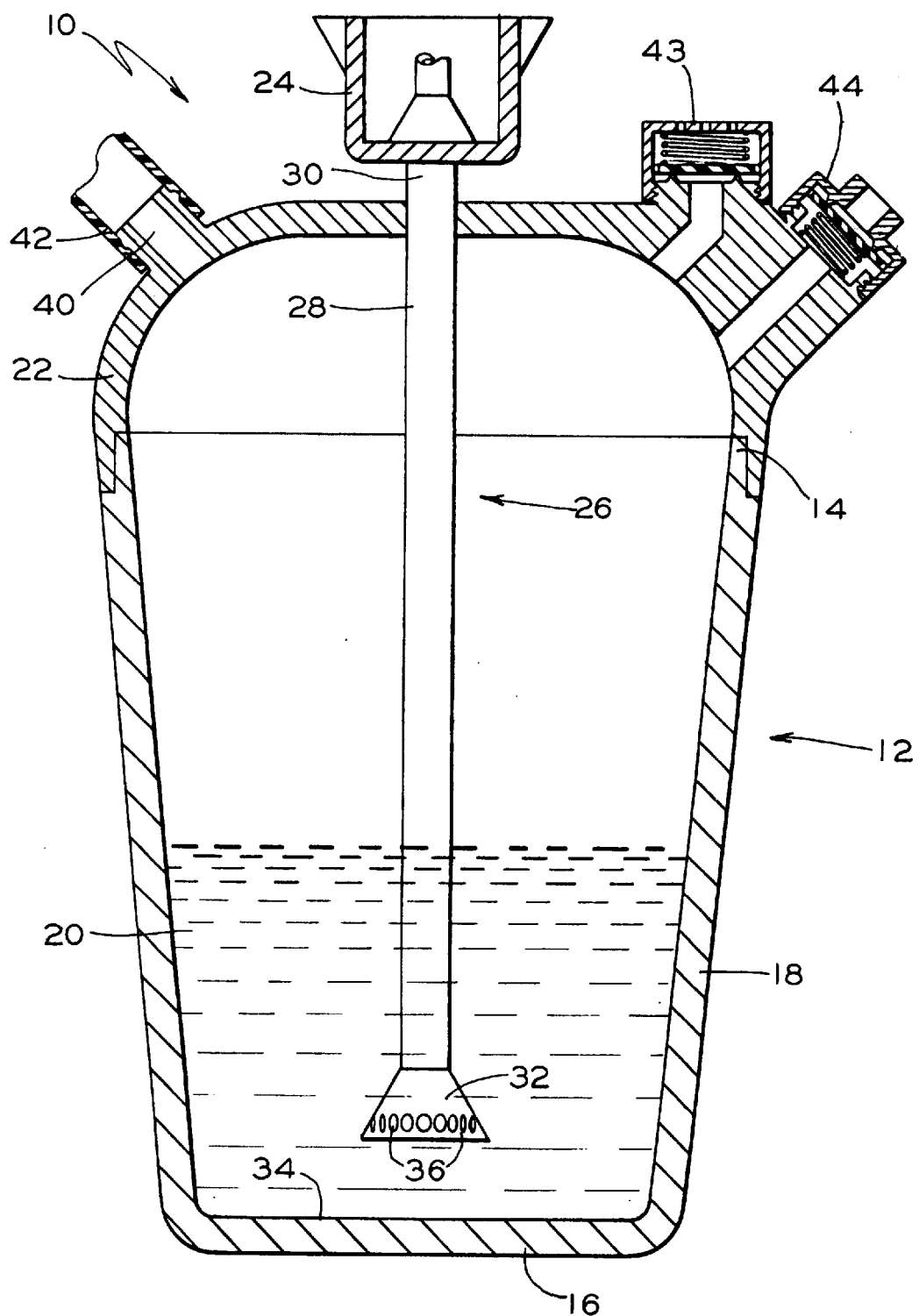
FIG. 4 is a cross-sectional view of a bubble humidifier including a liquid valve inlet means wherein the lid and container member are integrally joined together.
Figure 5:
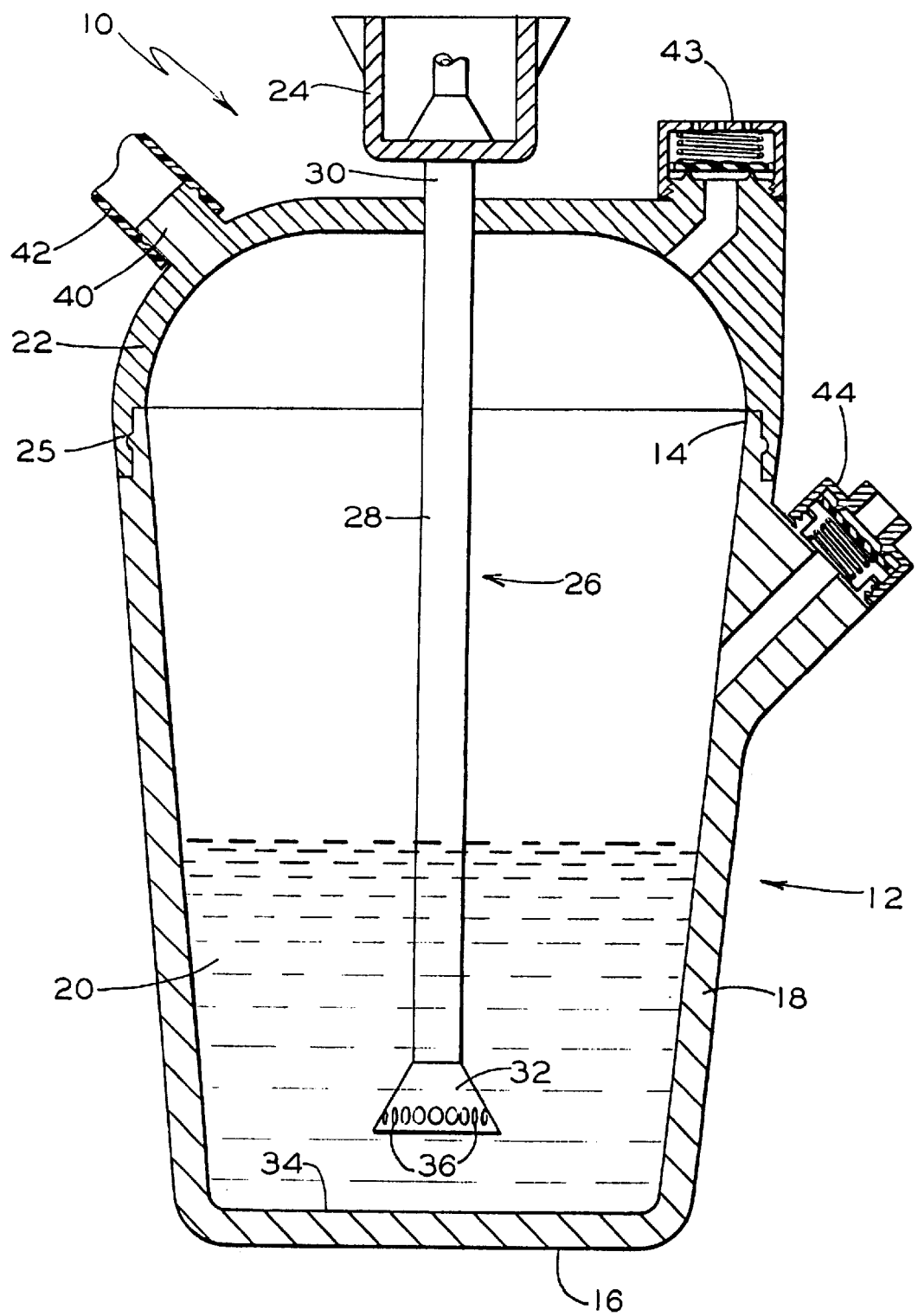
FIG. 5 is a cross-sectional view of a bubble humidifier including a liquid valve inlet means wherein the lid and container member are joined together by a snap fit.

A lid 22 is engageable with the container member 12. As shown in FIGS. 1–2 and 4, the lid 22 is engageable directly with the container member. FIG. 3 shows an embodiment including an insert member 50 positioned between the lid 22 and the container member 12. The insert member embodiment of FIG. 3 will be described more in detail below. The lid 22 may be engaged with the container member by any well known technique such as by a threaded engagement 23, a snap fit engagement 25, and the like. Alternatively, since the present invention allows for the addition of the liquid 20 directly into the container member 12 without removing the lid 22 from the container member 12, this lid 22 can be permanently secured with and/or formed integrally with the container member 12 as illustrated in FIG. 4.

The lid 22 has associated therewith a gas inlet means 24 such as a wing nut. This gas inlet means 24 is capable of being attached to a gas source, such as oxygen (not shown) via tubing. A means, generally designated as 26 is provided within the container member 12 for transporting gas fed from the gas inlet means 24 to the liquid 20 to cause the gas to become humidified. The means 26 for transporting gas within the container member 12 comprises a pipe 28 having a first end 30 and a second end 32, the first end 30 is associated with the gas inlet means 24 and the second end 32 is positioned adjacent an inner surface 34 of the bottom wall 16 of the container. This second end 32 of the pipe 28 includes openings or jets 36 through which gas from the gas inlet means 24 enters into the liquid 20 and forms bubbles.

A gas outlet means 40 is also associated with the lid 22. This gas outlet means 40 is capable of sending humidified gas to a patient via tubing 42 or any other well known type of transporting means.

Also provided in the lid 22 is a pressure relief valve or safety valve 43, as is well known in the art. This pressure relief valve 43 is provided to activate at an internal container pressure of greater than or equal to approximately 6 PSI. This pressure relief valve operates as a warning device to signal an obstruction downstream and typically emits a warning signal while venting any excess pressure from within the container to the atmosphere.

A valve means 44 is associated with the container member 12. This valve means 44 is typically a one way valve which enables the addition of a humidifying liquid 20, such as water, into the container member 12. The use of this valve means to add the humidifying liquid into the container eliminates the undesirable step of disassembling the lid 22 from the container member 12 in order to replenish the supply of humidifying liquid 20. This disassembly of the bubble humidifier 10 has several disadvantages as, enumerated above, especially in terms of the difficultly encountered by the patients to reassemble the bubble humidifier and the often unnecessary service calls having to be made by the home health care provider.

The valve means 44 can be any well known type of valve means such as a check, flapper, slide valve, and the like. Also, the valve means 44 can be attached and/or formed integrally with the lid 22, as illustrated in FIG. 1. Alternatively, the valve means 44 may be attached and/or formed integrally with the peripheral sidewall 18 of the container member 12, as illustrated in FIG. 2.

Figure 6:
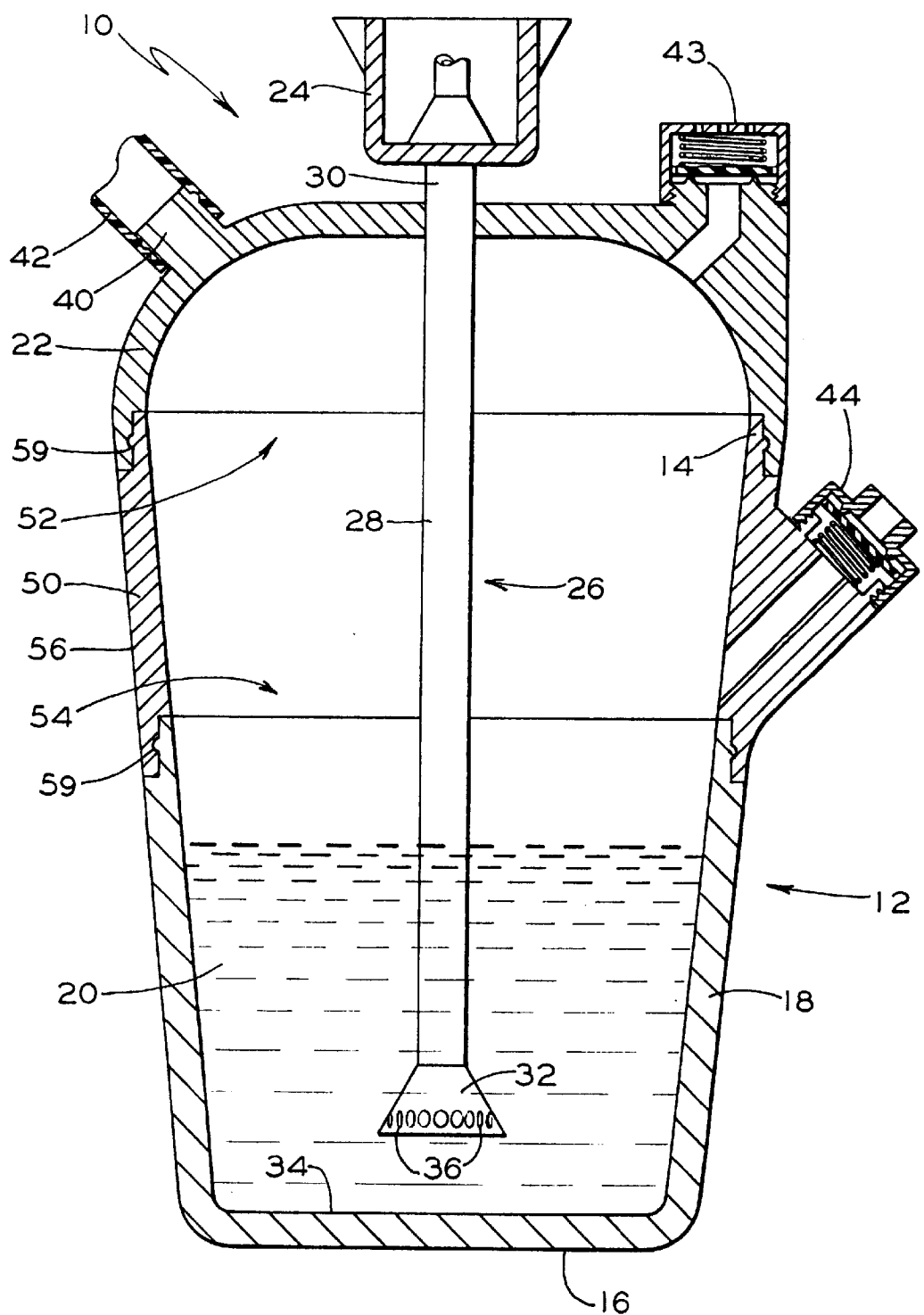
FIG. 6 is a cross-sectional view of a bubble humidifier including a liquid valve inlet means wherein the insert is joined to the lid and container portion by a snap fit.

Another alternative location for placement of the valve means 44 is illustrated in FIGS. 3 and 6. This embodiment includes the use of an insert member 50 having an open top portion 52, an open bottom portion 54, and at least one peripheral sidewall 56. This insert member is positioned between and engageable with the lid 22 and the top portion 14 of the container member 12. The insert member 50 is engageable with the lid 22 and container member 12 by any well known means, such as by a threaded engagement 58, a snap fitted engagement 59, and the like. Alternatively, the insert member 50 may be permanently secured with and/or formed integrally with either the lid 22 or the container member 12. The valve means 44 is positioned on the at least one peripheral sidewall 56 in a location that enables the addition of humidifying liquid 20 into the container member 12 without disassembly of such container member 12.

The use of the insert member 50 of the FIG. 3 embodiment allows currently used bubble humidifiers to be retrofitted to include the valve means 44 of the invention. The capability of retrofitting existing bubble humidifier units would result in significant cost savings to home health care providers, as well as to their patients.

Thus, the present invention has been described in such full, clear, concise and exact terms as to enable any person skilled in the art to which it pertains to make and use the same. It will be understood that variations, modifications, equivalents, and substitutions for components of the specifically described embodiments of the invention may be made by those skilled in the art without departing from the spirit and scope of the invention as set forth in the appended claims.

We claim:

1. A bubble humidifier for humidifying a gas sent to a patient, said humidifier comprising:

(a) a container member including a top portion, bottom wall, and at least one peripheral sidewall defining a chamber capable of containing a liquid therein;

(b) a lid sealingly engageable with one of said top portion of said container member and an insert disposed between said lid and said top portion of said container member;

(c) a gas inlet means associated with said lid, said gas inlet means capable of being attached to a gas source for positively supplying a gas through said gas inlet means;

(d) gas communication means within said container member and connected at an inlet thereof to said gas inlet means for transporting gas fed from said gas inlet means to a location disposed beneath a surface of said liquid to cause said gas to become humidified;

(e) a gas outlet means associated with said lid and disposed above said surface of said liquid, said gas outlet means capable of sending humidified gas to a patient; and (f) a one way valve means disposed on said humidifier to enable liquid to be added into the container member, said one way valve means capable of creating an air tight seal upon the application of gas within the bubble humidifier.

2. A bubble humidifier as recited in claim 1 wherein said valve means is one of a check, flapper, and slide valve.

3. A bubble humidifier as recited in claim 1 wherein said valve means is one of attached to and formed integrally with said lid.

4. A bubble humidifier as recited in claim 1 wherein said valve means is one of attached to and formed integrally with said container member.

5. A bubble humidifier as recited in claim 1 including a pressure relief valve associated with said lid.

6. A bubble humidifier as recited in claim 1 wherein said gas inlet means includes a wing nut.

7. A bubble humidifier as recited in claim 1 wherein said means within said container member for transporting gas comprises a pipe having a first and second end, said first end being associated with said gas inlet means and said second end being positioned above an inner surface of the bottom wall of the container.

8. A bubble humidifier as recited in claim 7 wherein said second end of said pipe includes openings or jets through which gas from said gas inlet means enters into the liquid and forms bubbles.

9. A bubble humidifier as recited in claim 1 wherein said gas outlet means is attached to tubing which carries the humidified gas to the patient.

10. A bubble humidifier as recited in claim 1 wherein said lid is threadedly engageable with said container member.

11. A bubble humidifier as recited in claim 1 wherein said lid has a snap fit with said container member.

12. A bubble humidifier as recited in claim 1 wherein said lid is one of permanently secured with and formed integrally with said container member.

13. A bubble humidifier as recited in claim 1 wherein said gas inlet means is capable of being attached to an oxygen source.

14. A bubble humidifier as recited in claim 1 wherein said gas communication means is capable of forming bubbles within said liquid so as to cause said gas to become humidified.

15. A method of retrofitting a bubble humidifier for humidifying a gas sent to a patient with a valve for allowing the application of liquid into the bubble humidifier, said bubble humidifier including a container member having a bottom wall, a top portion, and at least one peripheral sidewall and a lid having a top portion and a bottom portion, said top portion of said lid including a gas inlet valve and a gas outlet valve, said method comprising:

(a) providing an insert member having an open top portion, an open bottom portion, and at least one peripheral sidewall;

(b) providing said insert member between said top portion of said container member and said bottom portion of said lid;

(c) providing a valve on said at least one peripheral sidewall of said insert member so as to enable the application of liquid into the container member of the bubble humidifier.

16. A method of retrofitting a bubble humidifier as recited in claim 15 wherein said valve on said insert member is a one way valve.

17. A method of retrofitting a bubble humidifier as recited in claim 15 wherein said bottom portion of said insert member is capable of being one of threadedly engageable with and snap fitted with said top portion of said container member and said top portion of said insert member is capable of being one of threadedly engageable with and snap fitted with said bottom portion of said lid.

18. An insert member for use with a bubble humidifier, said bubble humidifier including a container member having a bottom wall, a top portion, and at least one peripheral sidewall and a lid having a top portion and a bottom portion, said top portion of said lid including a gas inlet valve and a gas outlet valve, said insert member comprising:

(a) a cylindrical member having an open top portion, an open bottom portion, and at least one peripheral sidewall, said open top portion of said cylindrical member being sealingly engageable with such bottom portion of such lid of such bubble humidifier and said bottom portion of said cylindrical member being sealing engageable with such top portion of such container member of such bubble humidifier; and (b) a valve means one of attached to and formed integrally with said peripheral sidewall of said cylindrical member, said valve means capable of allowing the addition of liquid into such container member of such bubble humidifier.

19. An insert member as recited in claim 18 wherein said valve means is a one way valve.

20. An insert member as recited in claim 18 wherein said valve means is one of a check, flapper, and slide valve.

21. An insert member as recited in claim 18 wherein said open top portion of said cylindrical member is one of threadedly engageable with and snap fitted with such bottom portion of such lid of such bubble humidifier and said bottom portion of said cylindrical member is one of threadedly engageable with and snap fitted with such top portion of such container member of such bubble humidifier.

22. A bubble humidifier for humidifying a gas sent to a patient, said humidifier comprising:

(a) a container member including a top portion, bottom wall, and at least one peripheral sidewall defining a chamber capable of containing a liquid therein;

(b) an insert member, having a top portion, a bottom portion, and at least one peripheral sidewall, said bottom portion of said insert member being positioned adjacent said top portion of said container member;

(c) a lid sealingly engageable with said top portion of said insert member;

(d) a gas inlet means associated with said lid, said gas inlet means capable of being attached to a gas source;

(e) gas communication means within said container member and connected at an inlet thereof to said gas inlet means for transporting gas fed from said gas inlet means to a location disposed beneath a surface of said liquid to cause said gas to become humidified;

(f) a gas outlet means associated with said lid and disposed above said surface of said liquid, said gas outlet means capable of sending humidified gas to a patient; and (g) valve means disposed on said humidifier to enable liquid to be added into the container member.

23. A bubble humidifier as recited in claim 22 wherein said valve means is one of attached to and formed integrally with said insert member.

\* \* \* \* \*